US008486698B2

(12) United States Patent
Black et al.

(10) Patent No.: US 8,486,698 B2
(45) Date of Patent: *Jul. 16, 2013

(54) DIFFERENTIATION OF BONE MARROW CELLS INTO NEURONAL CELLS AND USES THEREFOR

(75) Inventors: Ira B. Black, Skillman, NJ (US); Dale L. Woodbury, Piscataway, NJ (US); Darwin J. Prockop, New Orleans, LA (US); Emily Schwarz, River Ridge, LA (US)

(73) Assignees: University of Medicine and Dentistry of New Jersey, Newark, NJ (US); Philadelphia Health and Education Corporation, Philadelphia, PA (US)

( * ) Notice: Subject to any disclaimer, the term of this patent is extended or adjusted under 35 U.S.C. 154(b) by 350 days.

This patent is subject to a terminal disclaimer.

(21) Appl. No.: 11/849,870

(22) Filed: Sep. 4, 2007

(65) Prior Publication Data

US 2008/0131407 A1 Jun. 5, 2008

Related U.S. Application Data

(63) Continuation of application No. 10/213,526, filed on Aug. 6, 2002, now Pat. No. 7,279,331, which is a continuation of application No. PCT/US01/04282, filed on Feb. 9, 2001.

(60) Provisional application No. 60/181,850, filed on Feb. 11, 2000.

(51) Int. Cl.
*C12N 5/02* (2006.01)

(52) U.S. Cl.
USPC .................. 435/377; 435/368; 435/372

(58) Field of Classification Search
None
See application file for complete search history.

(56) References Cited

U.S. PATENT DOCUMENTS

| 5,639,618 A | 6/1997 | Gay |
| 6,090,622 A | 7/2000 | Gearhart et al. |
| 6,528,245 B2 * | 3/2003 | Sanchez-Ramos et al. ... 435/1.1 |
| 7,279,331 B2 * | 10/2007 | Black et al. .................. 435/368 |

FOREIGN PATENT DOCUMENTS

| WO | WO 95/00632 A1 | 1/1995 |
| WO | WO 96/30031 A1 | 10/1996 |
| WO | WO 99/43286 A2 | 9/1999 |
| WO | WO 99/56759 A1 | 11/1999 |
| WO | WO 01/83715 A2 | 11/2001 |

OTHER PUBLICATIONS

Correia et al., Annals of Medicine, 2005, vol. 37, pp. 487-498.*
Fernandez et al., Surgical Neurology, 2006, vol. 65, pp. 223-237.*
Neuhuber et al., Journal of Neuroscience Research, 2004, vol. 77, pp. 192-204.*
Abboud et al., "Peptide growth factors stimulate macrophage colony-stimulating factor in murine stromal cells", *Blood*, 78(1):103-109 (1991).
Azizi et al., "Engraftment and migration of human bone marrow stromal cells implanted in the brains of albino rats—similarities to astrocyte grafts", *Proc. Natl. Acad. Sci. USA*, 95(7):3908-3913 (1998).
Betz et al., "Activity-dependent fluorescent staining and destaining of living vertebrate motor nerve terminals", *J. Neurosci.*, 12(2):363-375 (1992).
Betz et al., "Optical analysis of synaptic vesicle recycling at the frog neuromuscular junction", *Science*, 255(5041):200-203 (1992).
Bjornson et al., "Turning brain into blood: a hematopoietic fate adopted by adult neural stem cells in vivo", *Science*, 283(5401):534-537 (1999).
Bruder et al., "Mesenchymal stem cells in osteobiology and applied bone regeneration", *Clin. Orthop. Relat. Res.*, 355S:S247-S256 (1998).
Caplan A.I., "Mesenchymal stem cells", *J. Orthop. Res.*, 9(5):641-650 (1991).
Carden et al., "Two-stage expression of neurofilament polypeptides during rat neurogenesis with early establishment of adult phosphorylation patterns", *J. Neurosci.*, 7(11):3489-3504 (1987).
Diefenbach et al., "Membrane recycling in the neuronal growth cone revealed by FM1-43 labeling", *J. Neurosci.*, 19(21):9436-9444 (1999).
Ferrari et al., "Muscle regeneration by bone marrow-derived myogenic progenitors", *Science*, 279(5356):1528-1530 (1998).
Flax et al., "Engraftable human neural stem cells respond to developmental cues, replace neurons, and express foreign genes", *Nature Biotech.*, 16(11):1033-1039 (1998).
Gage et al., "Isolation, characterization, and use of stem cells from the CNS", *Annu. Rev. Neurosci.*, 18:159-192 (1995).
Gage et al., "Survival and differentiation of adult neuronal progenitor cells transplanted to the adult brain", *Proc. Natl. Acad. Sci. USA*, 92(25):11879-11883 (1995).

(Continued)

*Primary Examiner* — Jim Ketter
(74) *Attorney, Agent, or Firm* — DLA Piper LLP (US)

(57) ABSTRACT

The present invention relates to methods of inducing differentiation of mammalian bone marrow stromal cells into neuronal cells by contacting marrow stromal cells with a neuronal differentiation-inducing compounds. Neuronal differentiation-inducing compounds of the invention include anti-oxidants such as, but not limited to, beta-mercaptoethanol, dimethylsulfoxide, butylated hydroxyanisole, butylated hydroxytoluene, ascorbic acid, dimethylfumarate, and n-acetylcysteine. Once induced to differentiate into neuronal cells, the cells can be used for cell therapy, gene therapy, or both, for treatment of diseases, disorders, or conditions of the central nervous system.

3 Claims, 9 Drawing Sheets

OTHER PUBLICATIONS

Horwitz et al., "Transplantability and therapeutic effects of bone marrow-derived mesenchymal cells in children with osteogenesis imperfecta", *Nature Med.*, 5(3):309-313 (1999).

Ishii et al., "Effects of 2-mercaptoethanol on survival and differentiation of fetal mouse brain neurons cultured in vitro", *Neurosci. Lett.*, 163(2):159-162 (1993).

Johansson et al., "Identification of a neural stem cell in the adult mammalian central nervous system", *Cell*, 96(1):25-34 (1999).

Kopen et al., "Marrow stromal cells migrate throughout forebrain and cerebellum, and they differentiate into astrocytes after injection into neonatal mouse brains", *Proc. Natl. Acad. Sci.*, 96(19):10711-10716 (1999).

Kosik et al., "MAP2 and tau segregate into dendritic and axonal domains after the elaboration of morphologically distinct neurites: an immunocytochemical study of cultured rat cerebrum", *J. Neurosci.*, 7(10):3142-3153 (1987).

Kuznetsov et al., "Factors required for bone marrow stromal fibroblast colony formation in vitro", *Br. J. Haematol.*, 97:561-570 (1997).

Lemiscka I., "Searching for Stem Cell Regulatory Molecules: Some General Thoughts and Possible Approaches", *Ann. N.Y. Acad. Sci.*, 872:274-288 (1999).

Lundberg et al., "Conditionally immortalized neural progenitor cell lines integrate and differentiate after grafting to the adult rat striatum. A combined autoradiographic and electron microscopic study", *Brain Res.*, 737(1-2):295-300 (1996).

Lundberg et al., "Survival, integration, and differentiation of neural stem cell lines after transplantation to the adult rat striatum", *Exp. Neurol.*, 145(2 Pt 1):342-360 (1997).

Majumdar et al., "Phenotypic and functional comparison of cultures of marrow-derived mesenchymal stem cells (MSCs) and stromal cells", *J. Cell Physiol.*, 176(1):57-66 (1998).

McKay R.D., "Brain stem cells change their identity", *Nature Med.*, 5(3):261-262 (1999).

Mena et al., "Glia protect fetal midbrain dopamine neurons in culture from L-DOPA toxicity through multiple mechanisms", *J. Neural Transmission*, 104(4-5):317-328 (1997).

Morshead et al., "Neural stem cells in the adult mammalian forebrain: a relatively quiescent subpopulation of subependymal cells", *Neuron*, 13(5):1071-1082 (1994).

Nakajima et al., "Retinoids (all-trans and 9-cis retinoic acid) stimulate production of macrophange colony-stimulating factor and granulocyte-macrophane colony-stimulating factor by human bone marrow stromal cells", *Blood*, 84(12):4107-4115 (1994).

Owens et al., "Stromal stem cells: marrow-derived osteogenic precursors", *Ciba Foundation Symp.*, 136, Chichester, U.K. pp. 42-60 (1988).

Pechumer et al., "Detection of neuron-specific gamma-enolase messenger ribonucleic acid in normal human leukocytes by polymerase chain reaction amplification with nested primers", *Lab. Invest.*, 69(6):743-749 (1993).

Pereira et al., "Cultured adherent cells from marrow can serve as long-lasting precursor cells for bone, cartilage, and lung in irradiated mice", *Proc. Natl. Acad. Sci. USA*, 92(11):4857-4861 (1995).

Pittenger et al., "Multilineage potential of adult human mesenchymal stem cells", *Science*, 284(5411):143-147 (1999).

Prockop D.J., "Marrow stromal cells as stem cells for nonhematopoietic tissues", *Science*, 276:71-74 (1997).

Reid et al., "Routine histological compared with immunohistological examination of bone marrow trephine biopsy specimens in disseminated neuroblastoma", *J. Clin. Pathol.*, 44(6):483-486 (1991).

Renfranz et al., "Region-specific differentiation of the hippocampal stem cell line HiB5 upon implantation into the developing mammalian brain", *Cell*, 66(4):713-729 (1991).

Reynolds et al., "Generation of neurons and astrocytes from isolated cells of the adult mammalian central nervous system", *Science*, 255(5052):1707-1710 (1992).

Richards et al., "De novo generation of neuronal cells from the adult mouse brain", *Proc. Natl. Acad. Sci. USA*, 89(18):8591-8595 (1992).

Rickard et al., "Isolation and characterization of osteoblast precursor cells from human bone marrow", *J. Bone Mineral Res.*, 11(3):312-324 (1996).

Sakai et al., "Tenascin-C induction in Whitlock-Witte culture: a relevant role of the thiol moiety in lymphoid-lineage differentiation", *Experimental Cell Research*, 217(2):395-403 (1995).

Sanchez-Ramos et al., "Adult bone marrow stromal cells differentiate into neural cells in vitro", *Experimental Neurology*, 164(2):247-256 (2000).

Sarnat et al., "Neuronal nuclear antigen (NeuN): a marker of neuronal maturation in early human fetal nervous system", *Brain Dev.*, 20(2):88-94 (1998).

Satomura et al., "Receptor tyrosine kinase expression in human bone marrow stromal cells", *J. Cell Physiol.*, 177:426-438 (1994).

Strelau et al., "Growth/differentiation factor-15/macrophage inhibitory cytokine-1 is a novel trophic factor for midbrain dopaminergic neurons in vivo", *J. Neurosci.*, 20(23):8597-8603 (2000).

Svendsen et al., "Long-term survival of human central nervous system progenitor cells transplanted into a rat model of Parkinson's disease", *Exp. Neurol.*, 148(1):135-146 (1997).

Tanaka et al., "Effect of platelet-derived growth factor on DNA synthesis and gene expression in bone marrow stromal cells derived from adult and old rats", *J. Cell Physiol.*, 164:367-375 (1995).

van Obberghen et al., "Human gamma enolase: isolation of a cDNA clone and expression in normal and tumor tissues of human origin", *J. Neurosci. Res.*, 19(4):450-456 (1988).

Vescovi et al., "bFGF regulates the proliferative fate of unipotent (neuronal) and bipotent (neuronal/astroglial) EGF-generated CNS progenitor cells", *Neuron*, 11(5):951-966 (1993).

Woodbury et al., "Adult rat and human bone marrow stromal cells differentiate into neurons", *J. Neurosci.*, 61(4):364-370 (2000).

Yan et al., "Ascorbic acid increases the yield of dopaminergic neurons derived from basic fibroblast growth factor expanded mesencephalic precursors", *J. Neurochem.*, 76(1):307-311 (2001).

Japan Society for Cell Biology / The Meeting Summaries and Lecture Abstracts (1993), vol. 46, pp. 215.

\* cited by examiner

FIG.5A
FIG.5B
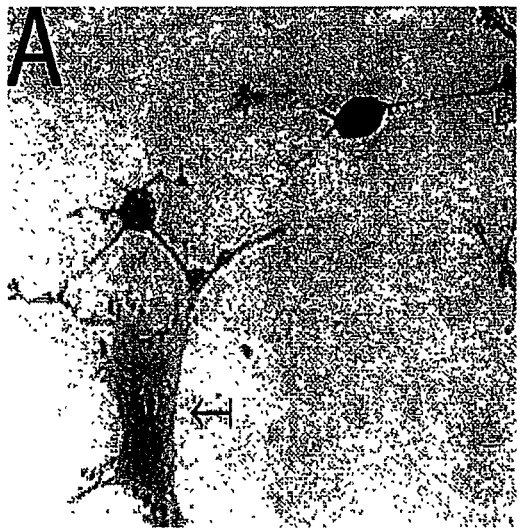 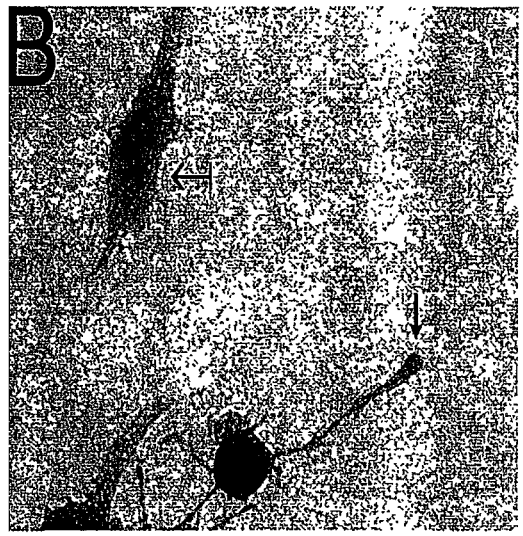
FIG.5C
FIG.5D
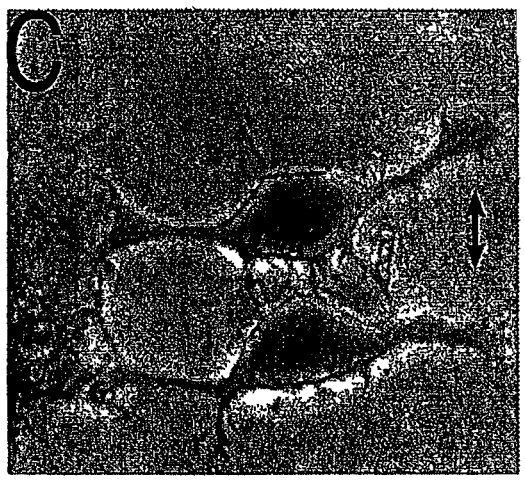 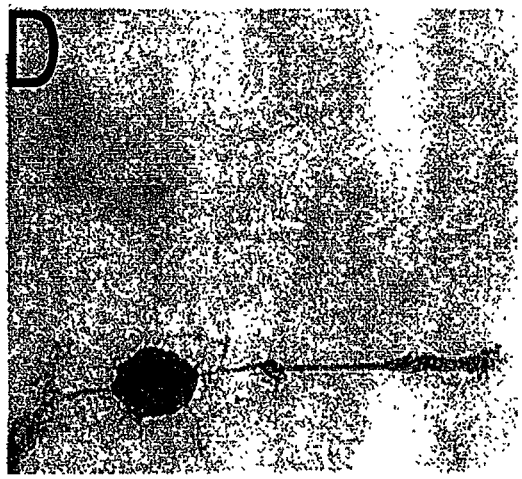

FIG. 6A
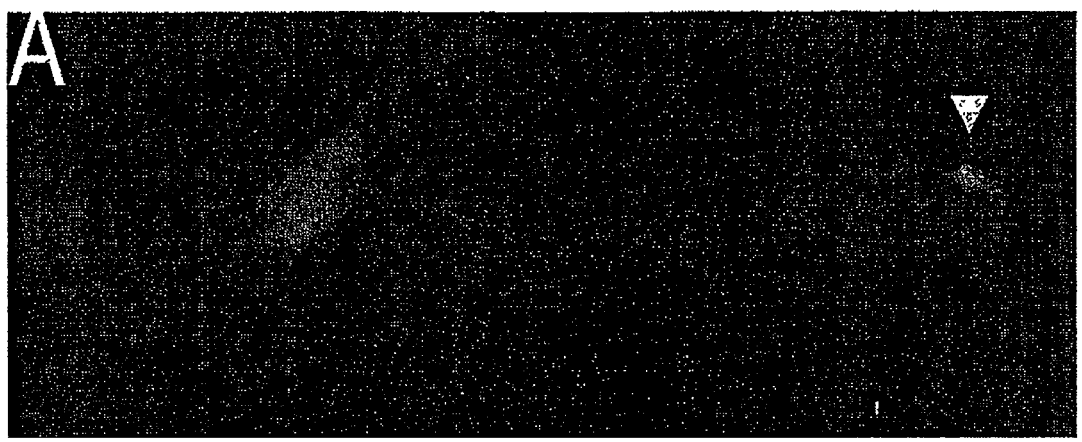
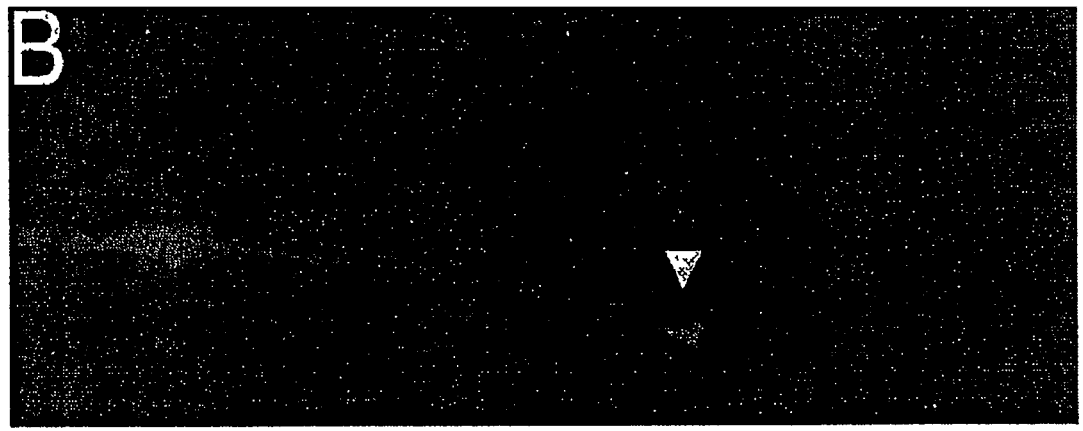
FIG. 6B

FIG. 8A
FIG. 8B
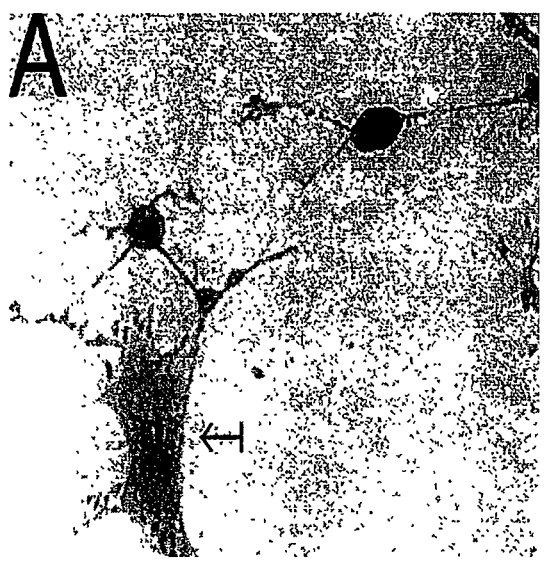
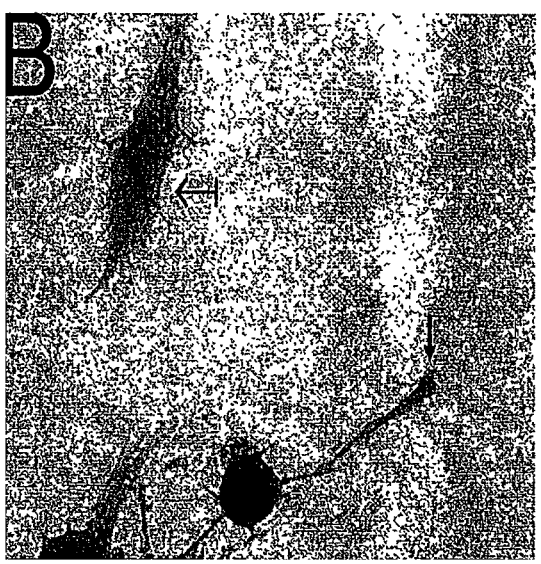
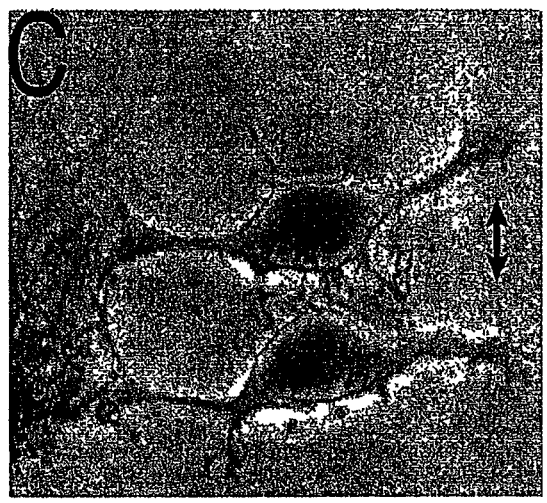
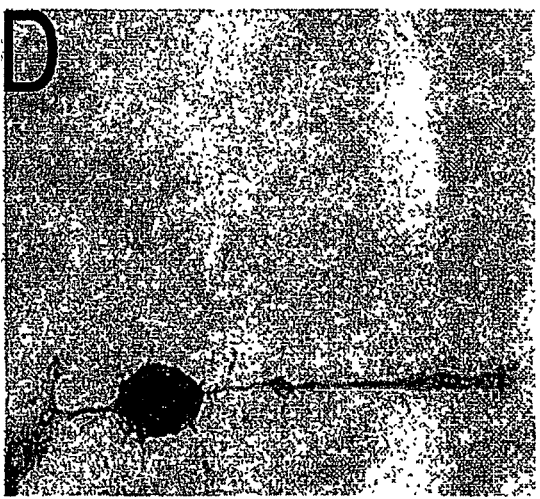
FIG. 8C
FIG. 8D

DIFFERENTIATION OF BONE MARROW CELLS INTO NEURONAL CELLS AND USES THEREFOR

This application is a continuation of U.S. patent application Ser. No. 10/213,526, filed Aug. 6, 2002, now allowed; which application is a continuation of International Application No. PCT/US01/04282, filed Feb. 9, 2001, now pending; which application claims priority from U.S. Provisional Application No. 60/181,850, filed Feb. 11, 2000; which applications are incorporated by reference herein in their entirety.

BACKGROUND OF THE INVENTION

Pluripotent stem cells have been detected in multiple tissues in the adult mammal, participating in normal replacement and repair, while undergoing self-renewal (Hay, 1966, Regeneration, Holt, Rinehart and Winston, New York; McKay, 1999, Nature Med. 5:261-262; Lemiscka, 1999, Ann. N.Y. Acad. Sci. 872:274-288; Owens and Friedenstein, 1988, Ciba Foundation Syp. 136, Chichester, U.K. pp. 42-60; Prockop, 1997, Science 276:71-74; Ferrari et al., 1998, Science 279:1528-1530; Caplan, 1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell Physiol. 176:57-66; Pittenger et al., 1999, Science 284:143-147). A subclass of bone marrow stem cells is one prototype, capable of differentiating into osteogenic, chondrogenic, adipogenic and other mesenchymal lineages in vitro (Owens and Friedenstein, 1988, Ciba Foundation Symp. 136, Chichester, U.K. pp. 42-60; Prockop, 1997, Science 276; 71-74; Ferrari et al., 1998, Science 279:1528-1530; Caplan, 1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell. Physiol. 176:57-66; Pittenger et al., 1999, Science 284:143-147). These pluripotent cells have been termed marrow stromal cells (MSCs), and recently have been used clinically to treat osteogenesis imperfecta (Horwitz et al., 1999, Nature Med. 5:309-313).

The recent discovery of stem cell populations in the central nervous system (CNS) has generated intense interest, since the brain has long been regarded as incapable of regeneration (Reynolds and Weiss, 1992, Science 255:1707-1710; Richards et al., 1992, Proc. Natl. Acad. Sci. USA 89:8591-8595; Morshead et al., 1994, Neuron 13:1071-1082). Neural stem cells (NSCs) are capable of undergoing expansion and differentiating into neurons, astrocytes and oligodendrocytes in vitro (Reynolds and Weiss, 1992, Science 255:1707-1710; Johansson et al., 1999, Cell 96:25-34; Gage et al., 1995, Annu. Rev. Neurosci. 18:159-192; Vescovi et al., 1993, Neuron 11:951-966). NSCs back transplanted into the adult rodent brain survive and differentiate into neurons and glia, raising the possibility of therapeutic potential (Lundberg et al., 1997, Exp. Neurol. 145:342-360; Lundberg et al., 1996, Brain Res. 737:295-300; Renfranz et al., 1991, Cell 66:713-729; Flax et al., 1998, Nature Biotech. 16:1033-1039; Gage et al., 1995, Proc. Natl. Acad. Sci. USA 92:11879-11883; Svendsen et al., 1997, Exp. Neurol. 148:135-146). However, the inaccessibility of NSC sources deep in the brain severely limits clinical utility. The recent report demonstrating that NSCs can generate hematopoietic cells in vivo suggests that stem cell populations may be less restricted than previously thought (Bjornson, 1999, Science 283:534-537).

Evidence that MSCs injected into the lateral ventricles of neonatal mice can differentiate to astrocytes and neurofilament-containing cells lends support to this contention (Kopen et al., 1999, Proc. Natl. Acad. Sci. 96:10711-10716).

However, although differentiation of MSCs into astrocytes and glial cells had been demonstrated (WO 99/43286), to date, there has been no method for inducing MSCs to differentiate into neuronal cells. Thus, despite the crucial need for obtaining neuronal cells for treatment of CNS diseases, disorders, and conditions, no method has been available for obtaining large numbers of neuronal cells without encountering the technical and ethical hurdles involved in obtaining human NSCs or fetal tissue. The present invention overcomes this need.

BRIEF SUMMARY OF THE INVENTION

The present invention includes a method of inducing differentiation of an isolated marrow stromal cell into a neuronal cell. The method comprises contacting the isolated marrow stromal cell with at least one neuronal differentiation-inducing compound. This induces differentiation of the isolated marrow stromal cell into a neuronal cell.

In one aspect, the isolated marrow stromal cell is a rat cell. Preferably, the isolated marrow stromal cell is a human cell.

In one aspect, the neuronal differentiation-inducing compound is an anti-oxidant. In another aspect, the anti-oxidant is selected from the group consisting of beta-mercaptoethanol, dimethylsulfoxide, butylated hydroxytoluene, butylated hydroxyanisole, ascorbic acid, dimethylfumarate, and n-acetylcysteine.

In yet another aspect, the anti-oxidant is beta-mercaptoethanol.

In another aspect, the anti-oxidant is dimethylsulfoxide. In yet another aspect the anti-oxidant is dimethylsulfoxide and butylated hydroxyanisole.

The neuronal differentiation-inducing compound is also a growth factor in another aspect. In a preferred aspect, the growth factor is selected from the group consisting of platelet-derived growth factor, fibroblast growth factor 2 and nerve growth factor.

The invention further includes a method of producing an isolated neuronal cell. The method comprises isolating a marrow stromal cell, contacting the marrow stromal cell with a neuronal differentiation-inducing compound wherein the compound induces the isolated marrow stromal cell to differentiate into an isolated neuronal cell, thereby producing an isolated neuronal cell.

In addition, the invention includes a method of treating a human patient having a disease, disorder or condition of the central nervous system. The method comprises obtaining a bone marrow sample from a human donor, isolating stromal cells from the bone marrow sample, inducing the stromal cells to differentiate into isolated neuronal cells, and administering the isolated neuronal cells to the central nervous system of the human patient. The presence of the isolated neuronal cells in the central nervous system of the human patient effects treatment of the disease, disorder or condition.

In one aspect, the disease, disorder or condition of the central nervous system is selected from the group consisting of Alzheimer's disease, Parkinson's disease, Huntington's disease, amyotrophic lateral sclerosis, a tumor, a trauma, elderly dementia, Tay-Sach's disease, Sandhoff's disease, Hurler's syndrome, Krabbe's disease, birth-induced traumatic central nervous system injury, epilepsy, multiple sclerosis, trauma, tumor, stroke, and spinal cord injury.

In another aspect, prior to administering the isolated neuronal cells, the isolated neuronal cells are transfected with an isolated nucleic acid encoding a therapeutic protein, wherein when the protein is expressed in the cells the protein serves to effect treatment of the disease, disorder or condition.

In an alternative aspect, the isolated neuronal cells are transfected with an isolated nucleic acid encoding a cytokine, a chemokine, a neurotrophin, another trophic protein, a growth factor, an antibody, or glioma toxic protein.

The present invention further includes a method of treating a human patient in need of neuronal cells. The method comprises obtaining marrow stromal cells from a human patient, propagating the marrow stromal cells in culture under conditions that induce their differentiation into neuronal cells, transplanting the neuronal cells into the human patient in need of the neuronal cells, thereby treating the human patient in need of neuronal cells.

The invention also includes an isolated neuronal cell made by the method of inducing differentiation of an isolated marrow cell into a neuronal cell. The method comprises contacting the isolated marrow stromal cell with at least one neuronal differentiation-inducing compound. The contact between the isolated marrow stromal cell and the neuronal differentiation-inducing compound induces differentiation of the isolated marrow stromal cell into the neuronal cell of the invention.

In an aspect, the neuronal cell made by this method is a rodent cell. In another aspect, the neuronal cell is a rat cell. In a preferred aspect, the neuronal cell made by this method is a human neuronal cell.

A preferred embodiment of the invention includes an isolated neuronal cell transfected with a therapeutic protein. The neuronal cell is isolated by the method of inducing differentiation of an isolated marrow cell into a neuronal cell recited above. The neuronal cell is then transfected with an isolated nucleic acid encoding a therapeutic protein that when expressed, will effect treatment of a disease, disorder, or condition of the central nervous system. In an aspect of the invention, the therapeutic protein encoded by the isolated nucleic acid is a cytokine, a chemokine, a neurotrophin, another trophic protein, a growth factor, an antibody, or glioma toxic protein.

The invention encompasses diseases, disorders, or conditions of the central nervous system including, but are not limited to, Alzheimer's disease, Parkinson's disease, Huntington's disease, amyotrophic lateral sclerosis, a tumor, a trauma, elderly dementia, Tay-Sach's disease, Sandhoff's disease, Hurler's syndrome, Krabbe's disease, birth-induced traumatic central nervous system injury, epilepsy, multiple sclerosis, trauma, tumor, stroke, and spinal cord injury.

In one aspect, the transfected neuronal cell made by the method of inducing differentiation of an isolated marrow stromal cell is a rat cell or a rodent cell. Preferably the transfected neuronal cell is a human cell.

The invention also includes an isolated neuronal cell produced by a method comprising isolating a marrow stromal cell and contacting it with a neuronal differentiation-inducing compound. This induces the isolated marrow stromal cell to differentiate into isolated neuronal cells.

A transfected isolated neuronal cell produced by isolating a marrow stromal cell and contacting it with a neuronal differentiation-inducing compound is also included in the invention. The isolated neuronal cell produced by this method is then transfected with an isolated nucleic acid encoding a therapeutic protein, that, when expressed in the neuronal cell, will effect treatment of a disease, disorder, or condition of the central nervous system.

In a preferred aspect, the therapeutic protein encoded by the isolated nucleic acid is a cytokine, a chemokine, a neurotrophin, another trophic protein, a growth factor, an antibody, or a glioma-toxic protein.

In an aspect of the present invention, the transfected neuronal cell produced by contacting a neuronal differentiation-inducing compound with a marrow stromal cell is a rat cell. In another aspect, the transfected neuronal cell is a rodent cell. In a preferred aspect, the transfected neuronal cell is a human cell.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 2, comprising FIG. 2A represents 0 minutes, FIG. 2B represents 30 minutes, FIG. 2C represents 60 minutes, FIG. 2E represents 120 minutes, FIG. 2F represents 150 minutes, FIG. 2G represents 180 minutes, and FIG. 2H represents 210 minutes. A flat rMSC in FIG. 2A is identified (▼) prior to differentiation. Retraction of cell body and process elaboration is evident with increasing time. The arrow in FIG. 2E indicates a second differentiating cell. Retracting neurite is indicated by (>). (Magnification=200×).

FIG. 3D is an image depicting a NSE-positive neuron elaborating a long process with evident varicosities (arrows). The data disclosed herein demonstrate that the neuronal cell body is in intimate contact with a transitional cell.

FIG. 5A is an image depicting expression of NF-M and tau by differentiating cells. Briefly, rMSC-derived neurons were immunostained to detect expression of NF-M using an anti-NF-M polyclonal antibody (Chemicon). The data disclosed herein demonstrate that cells that exhibit neuronal morphologies express NF-M in both cell bodies (arrow) and processes (*). Flat, undifferentiated rMSCs (>) do not stain for NF-M expression.

FIG. 5B is an image depicting that pre-adsorption of anti-NF-M antibody (Chemicon) with 20 micrograms of purified NF-M protein overnight at 4° C. eliminated staining of rMSC-derived neurons, indicating specificity of the NF-M staining.

FIG. 5C is an image depicting rMSC-derived neurons stained for expression of tau using anti-tau polyclonal antibody (Sigma Chemical Co., St. Louis, Mo.). The data disclosed herein demonstrate that cells displaying neuronal morphologies (arrows) stain dark brown for tau expression within the cell body and extending into the processes (*). Flat, undifferentiated rMSCs (>) do not express tau and are unstained. (Magnification=320×).

FIG. 5D is an image depicting rMSC-derived neurons stained for expression of tau using anti-tau polyclonal antibody (Sigma Chemical Co., St. Louis, Mo.). The data disclosed herein demonstrate that cells displaying neuronal morphologies (arrows) stain dark brown for tau expression within the cell body and extending into the processes (*). Flat, undifferentiated rMSCs (>) do not express tau and are unstained. (Magnification=320×).

FIG. 6A is an image depicting FM1-43 labeling of rMSC-derived neurons. The data disclosed herein demonstrate that rMSC-derived neurons depolarized using KCl demonstrate intense labeling of terminal putative growth cones (indicated by unfilled triangle).

FIG. 6B is an image depicting FM1-43 labeling of rMSC-derived neurons. The data disclosed herein demonstrate that rMSC-derived neurons depolarized using KCl demonstrate intense labeling of terminal putative growth cones (indicated by unfilled triangle).

FIG. 8A is an image depicting differentiation of human MSCs. The data disclosed herein demonstrate that human MSCs differentiate into neurons and express high levels of NSE (dark brown). A lighter stained transitional cell (indicated by ↦) is depicted at lower left.

FIG. 8B is an image depicting that an NSE-positive hMSC-derived neuron elaborates a process exhibiting neuronal-like terminal bulb morphology.

FIG. 8C is an image depicting a phase-contrast image of paired NSE-positive neurons. The data disclosed herein demonstrate growth cone morphologies with filopodial extensions (double arrow). The image is enlarged 50% to show detail.

FIG. 8D is an image depicting that hMSC-derived neurons stain positive for NF-M. (Magnification=320×).

FIG. 9, comprising FIGS. 9A-9C demonstrate cells stained for nestin expression at 5 hours, 1 day, and 6 days, respectively. FIGS.

Figure 1C:
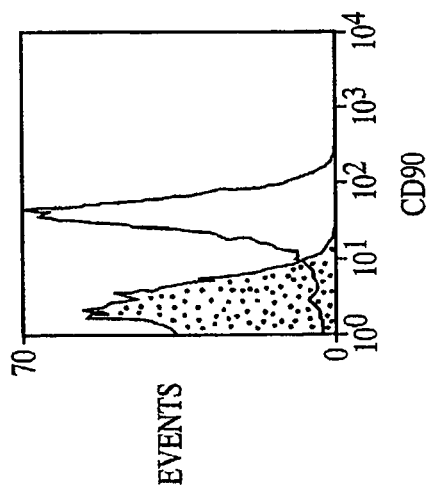
FIG. 1C is a graph depicting fluorescent cell sorting of passage 1 rMSCs using mouse monoclonal antibodies that specifically bind with cell surface marker CD90/Thy-1/CD90.1/Thy1.1 (Pharmingen) (unfilled peaks). The secondary antibody is anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis. The data disclosed herein demonstrate that the fluorescence intensity is greater (shifted to the right) when rMSCs are incubated with CD90 antibody (unfilled), as compared to control antibody (filled), indicating that the vast majority of cells in the rMSC cultures express CD90, consistent with their undifferentiated state.

9D-9F represent cells stained for trkA expression at 5 hours, 1 day, and 6 days, respectively. (Magnification=320×).

DETAILED DESCRIPTION OF THE INVENTION

The invention is based on the discovery that contacting marrow stromal cells with a neural-differentiation inducing agent mediates differentiation of the cells into neuronal-like cells expressing a variety of neuron-specific markers (e.g., NeuN, neurofilament-M, neuron-specific enolase [NSE], tau, nestin, trkA, and the like). The cells exhibit other neuron-like phenotypic characteristics such as, but not limited to, spherical and refactile cell bodies exhibiting typical neuronal perikaryal appearance, cell bodies extending long processes terminating in growth cones and filopodia typical of neurons, and labeling of the growth cones by the fluorescent dye FM1-43, which typically labels neuronal transmitter release and synaptic vesicle recycling. Thus, the methods disclosed herein induce marrow stromal cell differentiation into neuronal cells. Such methods are crucial in the development of cell-based therapeutics for treatment of central nervous system (CNS) disorders, diseases or conditions. Indeed, prior to the present invention, the lack of source of neuronal cells, which can be introduced into the CNS of a human patient, has severely impeded the development of CNS therapeutics.

Description

The invention includes a method of inducing an isolated marrow stromal cell to differentiate into an isolated neuronal cell. Embodiments of the method of the invention are described in the Examples section herein. Generally, cells are isolated from a donor, stromal cells are obtained therefrom, usually using a cell-sorting method, and the stromal cells are subsequently cultured in vitro. The donor may be a rat, for example, or the donor may be a human. The invention is intended to encompass a mammalian donor and should not be limited to the specific donors disclosed herein.

To induce the neuronal phenotype, the cells are pre-treated with an effective amount of a neuronal differentiation-inducing compound which is introduced into the cell culture for a period of time. The length of time may vary according to the precise method being contemplated and should not be construed as limiting the invention in any way. After pre-treatment exposure to the neuronal differentiation inducing compound, the cells are transferred to a serum-free medium containing an amount of the same neuronal differentiation-inducing compound. Neuronal morphology is evident within about an hour, see FIG. 2 for example, and the morphology becomes more evident steadily over time. Neuronal marker expression is also apparent within about 30 minutes after treatment. Neuronal cells so differentiated also eventually express several protein markers, including but not limited to, tyrosine hydroxylase, tubulin, choline acetyltransferase, synaptophysin, and TOAD, which are all proteins necessarily associated with neurons and neuronal processes.

These newly differentiated neuronal cells are useful in treating patients afflicted with diseases of the cholinergic and catecholaminergic systems, and more generally, patients afflicted with diseases of the central nervous system.

In one embodiment of the invention, antioxidants serve as the neuronal differentiation-inducing compounds, including but not limited to, beta-mercaptoethanol, dimethylsulfoxide, butylated hydroxytoluene, butylated hydroxyanisole, ascorbic acid, dimethylfumarate, and n-acetylcysteine. Particularly preferred embodiments as demonstrated in the Examples section herein disclosed, include beta-mercaptoethanol, dimethylsulfoxide and a combination of dimethylsulfoxide and butylated hydroxyanisole as the favored antioxidants. However, the invention is not limited to those antioxidants disclosed herein and should be construed to include all antioxidants, as well as other compounds which induce neuronal differentiation of marrow stromal cells.

The invention also contemplates use of growth factors as the neuronal differentiation-inducing compounds in the method of inducing differentiation of MSCs to neuronal cells. Such growth factors include, but are not limited to fibroblast growth factor 2, platelet-derived growth factor, and nerve growth factor, as well as related agents.

Neuronal identity can be confirmed by staining the differentiated neuronal cells for detection of neuron-specific markers. Examples of such markers are neurofilament-M (NF-M), tau protein, Neu-N, neuron-specific enolase (NSE), nestin, and trkA. Progressive differentiation of the marrow stromal cell to the neuronal cell corresponds with an increase in each of these markers, indicating that neuronal cells are produced. Further characterization can be accomplished using known immunocytochemical and antibody techniques. For example, immunocytochemical analysis of these neuronal cells reveals that the cells also express proteins that are associated with naturally-differentiated neurons. Such proteins include, but are not limited to tubulin, TOAD, and synaptophysin. Antibody detection of choline acetyltransferase and tyrosine hydroxylase may also be assessed.

It is apparent from the data disclosed herein that it is possible to differentiate isolated marrow stromal cell into neuronal cells in vitro. Neuronal cells so differentiated are useful in treating patients afflicted with any of a wide variety of central nervous system diseases, disorders, or conditions.

The invention also includes a method for producing an isolated neuronal cell from isolated marrow stromal cells. The method comprises differentiating an isolated marrow stromal cell in the same general manner as recited above, thereby producing an isolated neuronal cell.

The isolated neuronal cell recited in both of the methods above may be transfected with an isolated nucleic acid encoding a therapeutic protein. The therapeutic protein, when expressed, will treat a patient having a disease, disorder, or condition of the central nervous system.

A wide plethora of beneficial proteins are well-known in the art and are set forth in, for example, WO 96/30031 and WO 99/43286. Such examples include, but are not limited to, cytokines, chemokines, neurotrophins, other trophic proteins, growth factors, antibodies, and glioma toxic protein. When the transfected neuronal cells encoding such proteins are administered to a patient, the neuronal cells will beneficially influence cells which are already present in the central nervous system. For example, transfected neuronal cells which are introduced into the central nervous system may be used to repair any central nervous system damage, and/or to combat tumors of the central nervous system.

International patent applications WO 96/30031 and WO 99/43286 also describe use of MSCs in therapies for a wide variety of CNS diseases, disorders, or conditions, which include, but are not limited to, genetic diseases of the CNS (e.g., Tay-Sach's, Sandhoff's disease, Hurler's syndrome, Krabbe's disease), birth-induced traumatic CNS injury, adult CNS diseases, disorders or conditions (e.g., Parkinson's, Alzheimer's, and Huntington's diseases, elderly dementia, epilepsy, amyotropic lateral sclerosis, multiple sclerosis, trauma, tumors, stroke, and the like) and degenerative diseases and traumatic injury of the spinal cord.

Among neonates and children, transfected neuronal cells may be used for treatment of a number of genetic diseases of the central nervous system, including, but not limited to, Tay-Sachs disease and the related Sandhoff's disease, Hurler's syndrome and related mucopolysaccharidoses and Krabbe's disease. To varying extents, these diseases also produce lesions in the spinal cord and peripheral nerves and they also have non-neurological effects. While the non-neurological effects of these diseases may be treatable by bone marrow transplantation, the central nervous system effects do not improve despite bone marrow transplantation. The method of the present invention is useful to address the central nervous system effects of these types of diseases. In addition, in neonates and children, head trauma during birth or following birth is treatable by introducing these neuronal cells directly into the central nervous system of the children. Central nervous system tumor formation in children is also treatable using the methods of the present invention.

Adult diseases of the central nervous system are also treatable by administering isolated neuronal cells to the adult. Such adult diseases include but are not limited to, Parkinson's disease, Alzheimer's disease, spinal cord injury, stroke, trauma, tumors, degenerative diseases of the spinal cord such as amyotropic lateral sclerosis, Huntington's disease and epilepsy. Treatment of multiple sclerosis is also contemplated.

Treatment of spinal cord injuries is also possible using the method of the present invention. Prior art methods of treating spinal cord injuries involve using fibroblast cells to deliver neurotrophins to the site of spinal cord lesions in animals. The neurotrophins, delivered in this manner, reduce the lesion or otherwise treat the injury. However, fibroblasts produce large amounts of collagen, causing fibrosis at the site of the lesion, thus negating the beneficial effects of the treatment. Delivery of neurotrophins to spinal cord lesions using transfected neuronal cells is advantageous over prior art methods because neuronal cells do not produce large amounts of collagen and therefore should not cause fibrosis.

The invention further includes a method of treating a human patient having a disease, disorder, or condition of the central nervous system by administering the differentiated neuronal cells of the invention to the central nervous system of the patient. Methods of treating a human patient using MSCs are described in WO 96/30031 and WO 99/43286, which are incorporated by reference as if set forth in their entirety herein. Methods of administering differentiated neuronal cells to a patient are identical to those used for MSCs as described in WO 96/30031 and WO 99/43286. The methods encompass introduction of an isolated nucleic acid encoding a beneficial protein into differentiated neuronal cells and also encompass using differentiated neuronal cells themselves in cell-based therapeutics where a patient is in need of the administration of such cells. The differentiated neuronal cells are preferably administered to a human, and further, the neuronal cells are preferably administered to the central nervous system of the human. In some instances, the differentiated neuronal cells are administered to the corpus striatum portion of the human brain. The precise site of administration of the neuronal cells will depend on any number of factors, including but not limited to, the site of the lesion to be treated, the type of disease being treated, the age of the human and the severity of the disease, and the like. Determination of the site of administration is well within the skill of the artisan versed in the administration of cells to mammals.

The mode of administration of the differentiated neural cells to the central nervous system of the human may vary depending on several factors including but not limited to, the type of disease being treated, the age of the human, whether the neuronal cells have isolated DNA introduced therein, and the like. An example of administration of neuronal cells directly into brain tissue is provided herein in the experimental details section. Generally, cells are introduced into the brain of a mammal by first creating a hole in the cranium through which the cells are passed into the brain tissue. Cells may be introduced by direct injection, by using a shunt, or by any other means used in the art for the introduction of compounds into the central nervous system.

Definitions

The articles "a" and "an" are used herein to refer to one or to more than one (i.e. to at least one) of the grammatical object of the article. By way of example, "an element" means one element or more than one element.

As used herein, "central nervous system" should be construed to include brain and/or the spinal cord of a mammal. The term may also include the eye and optic nerve in some instances.

As used herein, "stromal cells", "isolated marrow stromal cells", and "MSCs" are used interchangeably and are meant to refer to the small fraction of cells in bone marrow which can serve as stem cell-like precursors of osteocytes, chondrocytes, and adipocytes and which are isolated from bone marrow by their ability adhere to plastic dishes. Marrow stromal cells may be derived from any animal. In some embodiments, stromal cells are derived from primates, preferably humans.

As used herein, the term "anti-oxidant" is meant to refer to those substances that inhibit oxidation or reactions promoted by oxygen or peroxides. Examples of anti-oxidants include, but are not limited to, beta-mercaptoethanol, dimethylsulfoxide, butylated hydroxytoluene, butylated hydroxyanisole, ascorbic acid, dimethylfumarate, and n-acetylcysteine.

As used herein, the terms "beneficial protein" and "therapeutic protein" are used interchangeably and are meant to refer to a protein which can compensate for the protein encoded by a defective gene and/or insufficient gene expression that is causally linked to the disease or symptoms of the disease, disorder or condition characterized by a gene defect. The presence of the protein alleviates, reduces, prevents or causes to be alleviated, reduced or prevented, the causes and/or symptoms that characterize the disease, disorder or condition.

As used herein, a disease, disorder or condition which can be treated with a beneficial or therapeutic protein is meant to refer to a disease, disorder or condition that can be treated or prevented by the presence of a protein which alleviates, reduces, prevents or causes to be alleviated, reduced or prevented, the causes and/or symptoms that characterize the disease, disorder or condition. Diseases, disorders and conditions which can be treated with a beneficial protein include diseases, disorders and conditions characterized by a gene defect as well as those which are not characterized by a gene defect but which nonetheless can be treated or prevented by the presence of a protein which alleviates, reduces, prevents or causes to be alleviated, reduced or prevented, the causes and/or symptoms that characterize the disease, disorder or condition.

The term "isolated nucleic acid" should be construed to refer to a nucleic acid sequence, or segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

As used herein, "transfected cells" is meant to refer to cells to which a gene construct has been provided using any technology used to introduce nucleic acid molecules into cells such as, but not limited to, classical transfection (calcium phosphate or DEAE dextran mediated transfection), electroporation, microinjection, liposome-mediated transfer, chemical-mediated transfer, ligand mediated transfer or recombinant viral vector transfer.

The term "differentiation" as used herein, should be construed to mean the induction of a differentiated phenotype in an undifferentiated cell by coculturing the undifferentiated cell in the presence of a substantially homogeneous population of differentiated cells, in the presence of products of differentiated cells or in the presence of an inducer of cell differentiation.

The term "neuronal cell" as used herein should be construed to mean an MSC differentiated such that it expresses at least one of the following neuronal markers: neuron-specific enolase (NSE), NeuN, neurofilament M, or tau protein.

The term "neuron" as used herein should be construed to mean a nerve cell capable of receiving and conducting electrical impulses from the central nervous system. A nerve cell or "neuron" typically comprises a cell body, an axon, axon terminals, and dendrites.

The term "neuronal differentiation-inducing compound" is meant to refer to those compounds capable of inducing differentiation of a stromal cell into a neuronal cell. These compounds include, but are not limited to antioxidants, trophic factors, and growth factors.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The experiments presented in this example may be summarized as follows.

Bone marrow stromal cells exhibit multiple traits of a stem cell population. They can be greatly expanded in vitro, and induced to differentiate into multiple mesenchymal cell types (see, e.g., WO 96/30031; WO 99/43286). However, differentiation to non-mesenchymal fates has not been demonstrated. Here, adult rat stromal cells were expanded as undifferentiated cells in culture for more than 14 passages, indicating their proliferative capacity. Further, a novel treatment protocol induced the stromal cells to exhibit a neuronal phenotype, expressing various neuron-specific markers, i.e., neuron-specific enolase (NSE), NeuN, neurofilament-M, tau, nestin, and trkA.

Moreover, the retractile cell bodies of the treated cells extended long processes terminating in growth cones and filopodia typical of neuronal cells. The fluorescent dye, FM1-43, labeled growth cones, consistent with transmitter release and synaptic vesicle recycling by the treated cells. Clonal cell lines, established from single cells, proliferated, yielding both undifferentiated and cells exhibiting a neuronal phenotype.

Human marrow stromal cells treated using the novel protocol disclosed herein differentiated into neurons similarly to rMSCs demonstrating that the protocol is not limited to rodent stromal cells. Consequently, the data disclosed herein demonstrate, for the first time, that mammalian marrow stromal cells can be induced to overcome their mesenchymal commitment, and can constitute an abundant and accessible cellular reservoir for the treatment of a variety of neurologic diseases, disorders or conditions.

The Materials and Methods used in the experiments presented in this example are now described.

Cell Culture

Rat MSCs were originally cultured in alpha-Modified Eagle's Medium (alpha-MEM) supplemented with 20% FBS, 2 mM L-glutamine, 100 units per milliliter penicillin, 100 milligrams per milliliter streptomycin and 25 nanograms per milliliter amphotericin B. For each passage the cells were plated at about 8,000 cells per square centimeter and grown to confluency. At passage 6 the cells were transferred to DMEM (pH 8.0)/20% FBS without additional supplementation, and maintained beyond passage 14. The rat MSCs were obtained with a protocol and procedures approved by the Institutional IACUC. The human samples were obtained from volunteers with informed consent and according to a protocol approved by the Institutional Review Board.

Western Blot

Thirty milligrams of protein extract from untreated (U) and BME-induced (I) rMSC cultures was separated on a 4%-20% gradient acrylamide gel and electrophoretically transferred to a nylon membrane. The Western blot was probed for tubulin expression using an anti-tubulin monoclonal antibody (Sigma Chemical. Co., St. Louis, Mo.) followed by secondary antibody conjugated with horse radish peroxidase (HRP). Color development was performed using enhanced chemiluminescence reagents (Amersham, Piscataway, N.J.). The blot was then stripped and probed for NSE expression using anti-NSE polyclonal antibody (ICN). Again, the secondary antibodies were HRP-conjugated, and color was developed using ECL reagents.

Immunocytochemistry

Cultured rMSCs were fixed with 4% paraformaldehyde, incubated with primary antibody overnight at 4° C., incubated with secondary antibody for one hour, followed by exposure to avidin-biotin complex for one hour at 25° C. Diaminobenzidene (DAB) served as chromogenic substrate for HRP.

FM1-43 Labeling

Cultures were treated with DMSO/BHA in serum-free media (SFM) for approximately 4 hours. The cells were maintained for an additional 30 minutes in artificial cerebral spinal fluid (aCSF)/BHA. Cells were labeled in aCSF containing 1 millimolar FM1-43 and 75 mM KCl for 60 seconds. The labeling mixture was removed, the cultures were washed twice with aCSF, and the cells were incubated in aCSF for 60 minutes to reduce background staining. Cultures were fixed with 4% paraformaldehyde, and soaked for 24 hours in phosphate buffered saline (PBS) before analysis.

The Results of the experiments presented in this example are now described.

Stromal Cell Characterization

Figure 1B:
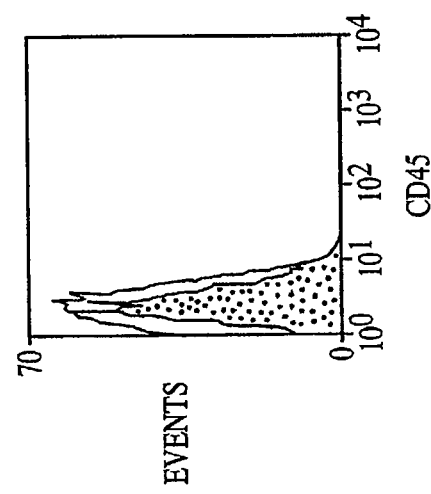
FIG. 1B is a graph depicting fluorescent cell sorting of passage 1 rMSCs using mouse monoclonal antibodies that specifically bind with cell surface marker CD45/leukocyte common antigen (Pharmingen) (unfilled peaks). The secondary antibody is anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis.
Figure 1A:
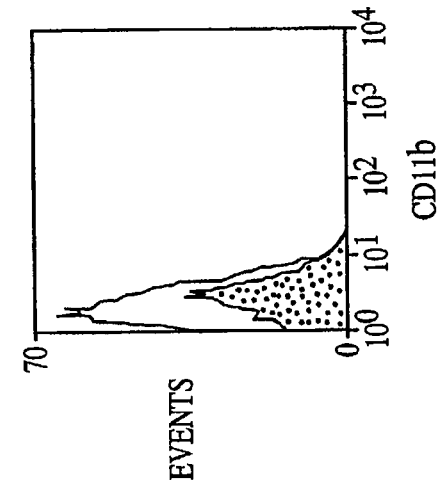
FIG. 1A is a graph depicting fluorescent cell sorting of passage 1 rMSCs using mouse monoclonal antibodies that specifically bind with cell surface marker CD11b (CD11/integrin alpha$_M$/Mac-1 alpha chain; Pharmingen, San Diego, Calif.) (unfilled peaks). The secondary antibody used was anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis.

Rat mesenchymal stromal cells (rMSCs) were isolated from the femurs of adult rats and propagated in vitro (Azizi et al., 1998, Proc. Natl. Acad. Sci. USA 95:3908-3913). The data disclosed in FIG. 1A demonstrate that the distribution of cells stained with antibody to CD 11b (unfilled) does not differ from that of isotype control (filled), indicating the rMSC cultures do not contain significant numbers of contaminating CD11b-expressing cells. Further, the data disclosed in FIG. 1B also demonstrate that the intensity of staining does not differ between CD45 antibody (unfilled) and control (filled) profiles, indicating that cultured rMSCs are not contaminated by CD45-expressing cells. Fluorescent cell sorting at passage one also demonstrated that the cells were negative for CD11b (FIG. 1A), and CD45 (FIG. 1B), which are cell surface markers associated with lymphohematopoietic cells. Therefore, there was no evidence of hematopoietic precursors in the cultures.

In contrast, the data disclosed herein demonstrate that rMSCs expressed CD90 (FIG. 1C), consistent with their undifferentiated state. At low plating densities rMSCs grew as a monolayer of large, flat cells. As the cells approached confluency, they assumed a more spindle-shaped, fibroblastic morphology. At the outset of the neuronal differentiation studies disclosed elsewhere herein, untreated rMSCs were further characterized by staining for the cell surface markers CD44 and CD71. Cells were positive for CD44 and CD71 expression, consistent with previous reports (Pittenger et al., 1999, Science 284:143-147; Bruder et al., 1998, Clin. Orthop. Relat. Res. 355S:S247-S256).

Neuronal Differentiation

Figure 2A:
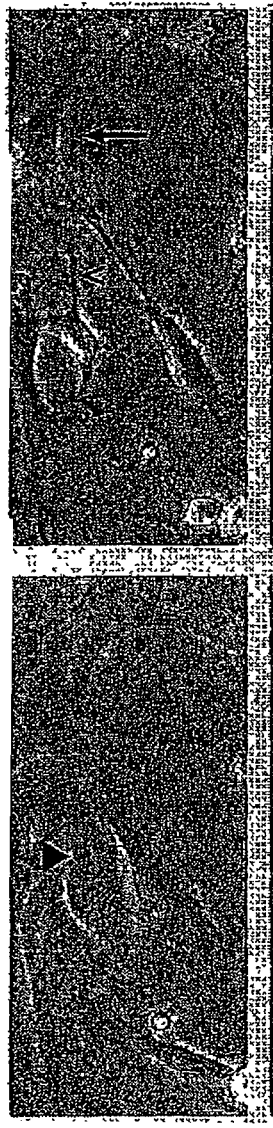
FIGS. 2A-2H, is an image depicting neuronal differentiation of rMSCs at various time points after treatment. Briefly, the neuronal differentiation protocol disclosed herein was initiated at 0 minutes and followed for 210 minutes.
Figure 2B:
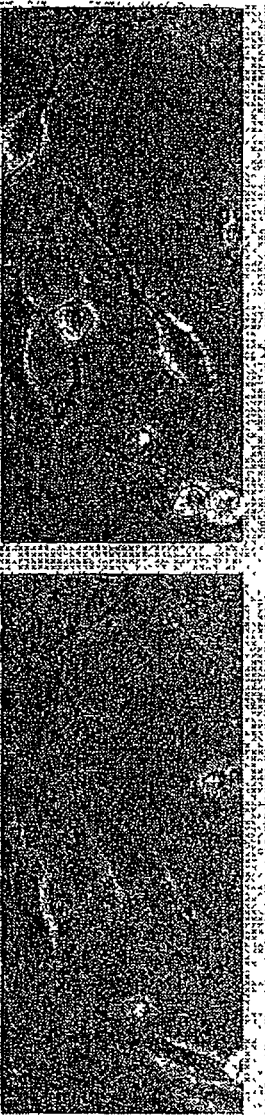
Figure 2C:
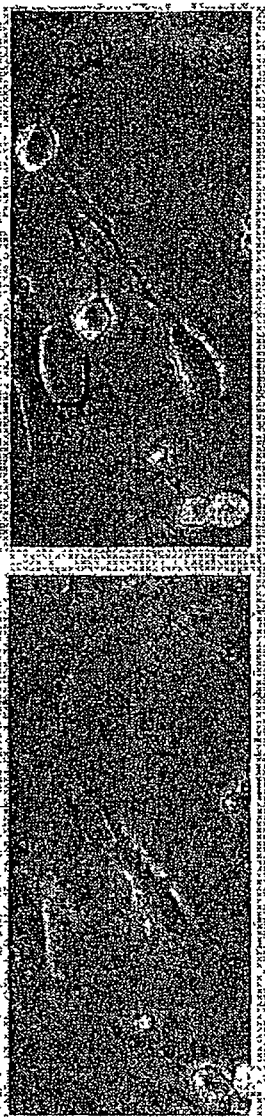
Figure 2D:
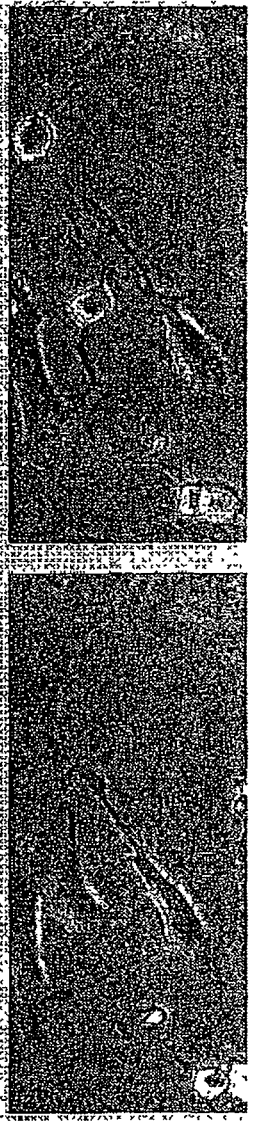
Figure 2E:
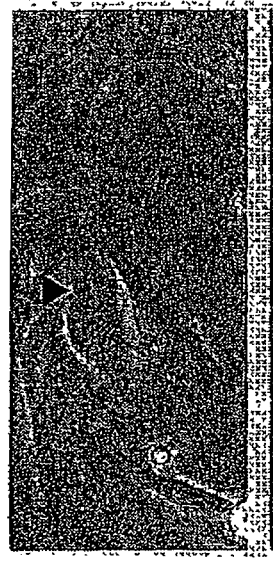
Figure 2F:
Figure 2G:
Figure 2H:

To induce the neuronal phenotype, rMSCs were initially maintained in sub-confluent cultures in media supplemented with 1 mM beta-mercaptoethanol (BME) for 24 hours. Under these conditions no changes in morphology were evident. To effect neuronal differentiation, the cells were transferred to serum-free medium containing 1-10 millimolar BME (SFM/BME). The percentage of cells adopting a neuronal morphology increased at higher BME concentrations, and was enhanced by BME pretreatment. Within 60 minutes of exposure to SFM/BME changes in morphology of some of the rMSCs were apparent (FIG. 2C). Responsive cells progressively assumed neuronal morphological characteristics over the first 3 hours. Initially, cytoplasm in the flat rMSCs retracted towards the nucleus, forming a contracted multipolar, cell body, leaving membranous, process-like extensions peripherally (0-90 minutes).

Treated cells exhibited increased expression of the neuronal marker NSE within 30 minutes of treatment. Over the subsequent 2 hours cell bodies became increasingly spherical and refractile, exhibiting a typical neuronal perikaryal appearance. Processes continued to elaborate, developing growth cone-like terminal expansions and filopodial extensions (see, e.g., FIGS. 2G and 2H). Cellular processes exhibited primary and secondary branches, and underwent dynamic growth. Retraction, as well as extension, was evident as demonstrated by the fact that the cell marked by an arrow at 120 minutes (FIG. 2E) was initially contacted by a neighboring process (marked by ">"), which retracted by 180 minutes (FIG. 2G), with loss of contact.

To further characterize potential neuronal differentiation, BME-treated cultures were stained to detect expression of the neuronal marker neuron-specific enolase (NSE). Unresponsive, flat rMSCs expressed very low, but detectable, levels of NSE protein, consistent with previous detection of minute amounts of protein and/or message in cells of bone marrow origin (Pechumer et al., 1993, Lab. Invest. 89:743-749; Reid et al., 1991, Clin. Pathol. 44:483-486; vanObberghen et al., 1988, J. Neurosci. Res. 19:450-456).

Figure 3A:
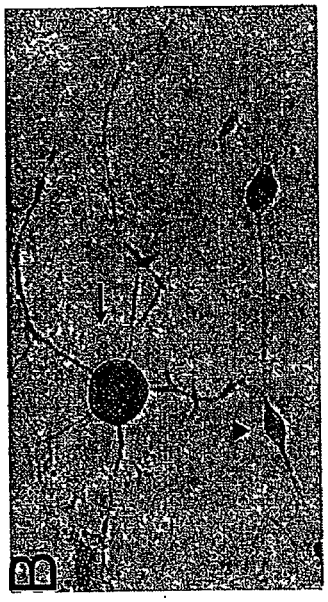
FIG. 3A is an image depicting neuron-specific enolase (NSE) expression in differentiating neurons using an anti- NSE polyclonal antibody (Polysciences, Warrington, Pa.). Briefly, undifferentiated rMSCs (indicated by a ">") retained flattened morphology and stained only slightly for NSE expression. rMSC-derived neurons (arrows) stained dark brown for NSE expression and displayed condensed cell bodies and highly branches processes. Transitional cells (↦) exhibited intermediate neuronal morphologies, with partially retracted cell bodies and light brown NSE staining.
Figure 3B:
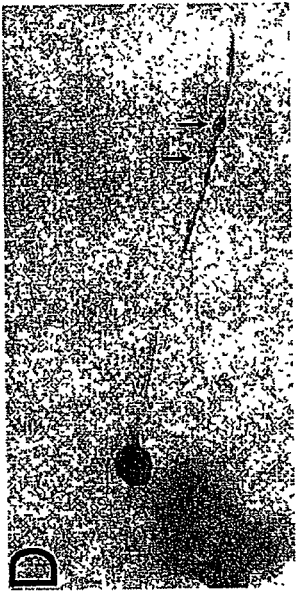
FIG. 3B is an image depicting that the morphologies of rMSC-derived neurons include simple bipolar (▼) and complex multipolar cells with highly branched processes (arrow). Intense NSE staining is evident in both neuronal cell types.
Figure 3F:
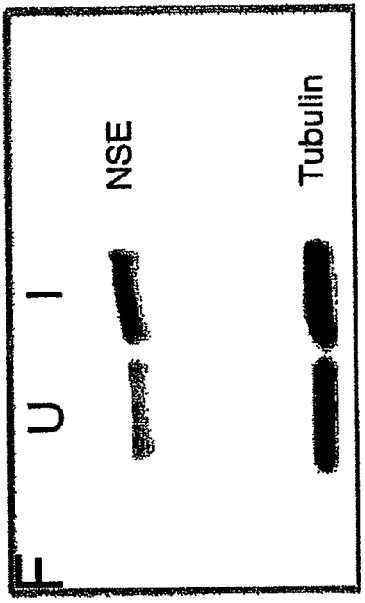
FIG. 3F is an image of a Western blot analysis disclosing expression of low levels of NSE in uninduced rMSCs (U). The data disclosed herein demonstrate that a significant increase in NSE expression is evident at 5 hours post BME treatment (I). Comparable levels of tubulin are detected in each lane, indicating equal loading of samples.
Figure 3C:
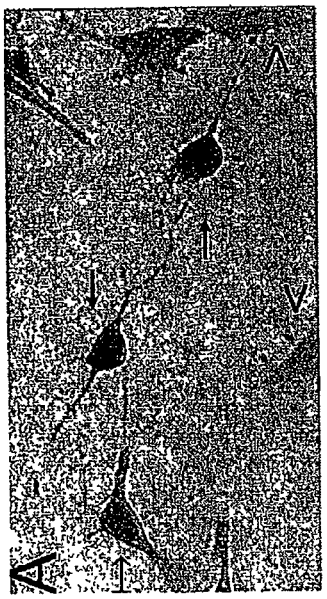
FIG. 3C is an image depicting that NSE-positive neurons displaying pyramidal morphologies are sometimes generated using the protocols disclosed elsewhere herein. Contact with a transitional cell (light brown) is maintained via a single unbranched process.
Figure 3D:
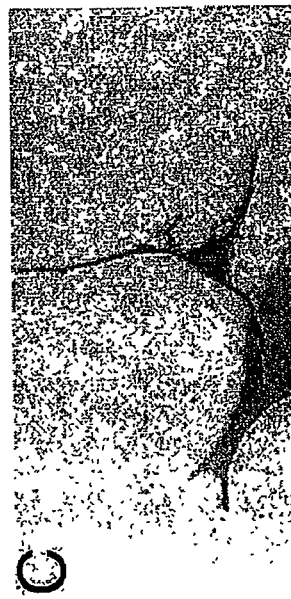
FIG. 3D represents 90 minutes.
Figure 3E:
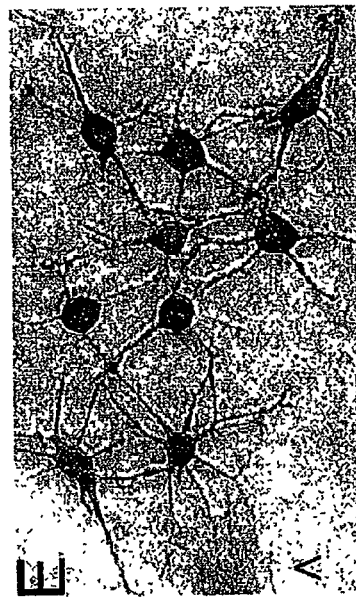
FIG. 3E is an image depicting that clusters of rMSC-derived neurons of varying morphologies form complex networks. The data disclosed herein demonstrate that an undifferentiated rMSC (>) is included within this meshwork of processes. (Magnification=320×).

Progressive transition of rMSCs to a neuronal phenotype coincided with increased expression of NSE (FIG. 3A). Cells that exhibited contracted cell bodies and processes stained dark brown for NSE expression (arrows), while flat, unresponsive rMSCs (>) displayed minimal NSE staining. Cells at intermediate stages in the differentiation sequence (↦) exhibited transitional morphologies and light brown staining, indicating synchrony of morphologic and molecular differentiation. rMSC-derived neurons displayed distinct neuronal morphologies (FIG. 3B), ranging from simple bipolar (▼) to large, extensively branched multipolar cells (arrow). Rare NSE-positive neurons exhibited pyramidal cell morphologies (FIG. 3C), while neurons elaborating long processes with evident varicosities (arrows) were more common (FIG. 3D). Clusters of differentiated cells exhibited intense NSE positivity, and processes formed extensive networks (FIG. 3E). Even within these clusters, typical, flat rMSCs (>) were only lightly stained, consistent with their undifferentiated state.

Western blot analysis (FIG. 3F) confirmed the expression of low levels of NSE protein in uninduced rMSCs. Induction of the neuronal phenotype resulted in a dramatic increase in NSE expression, consistent with the immunocytochemical data.

Figure 4B:
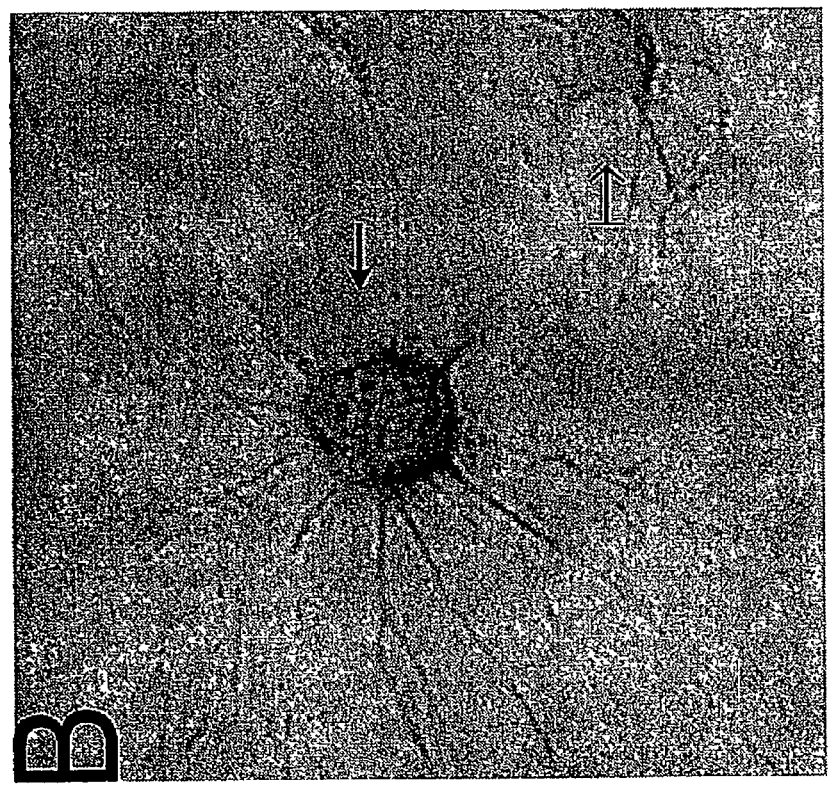
FIG. 4B is an image depicting NeuN expression in rMSC-derived neurons using a monoclonal anti-NeuN antibody (Chemicon). Briefly, the data disclosed herein demonstrate that NeuN can be detected in the nucleus and surrounding cytoplasm of rMSC-derived neurons (arrow). Further, the data disclosed herein demonstrate that anti-NeuN antibody staining does not extend into the processes of positive cells. The image further depicts that transitional cells (↦) and undifferentiated rMSCs (<) do not express NeuN.
Figure 4A:
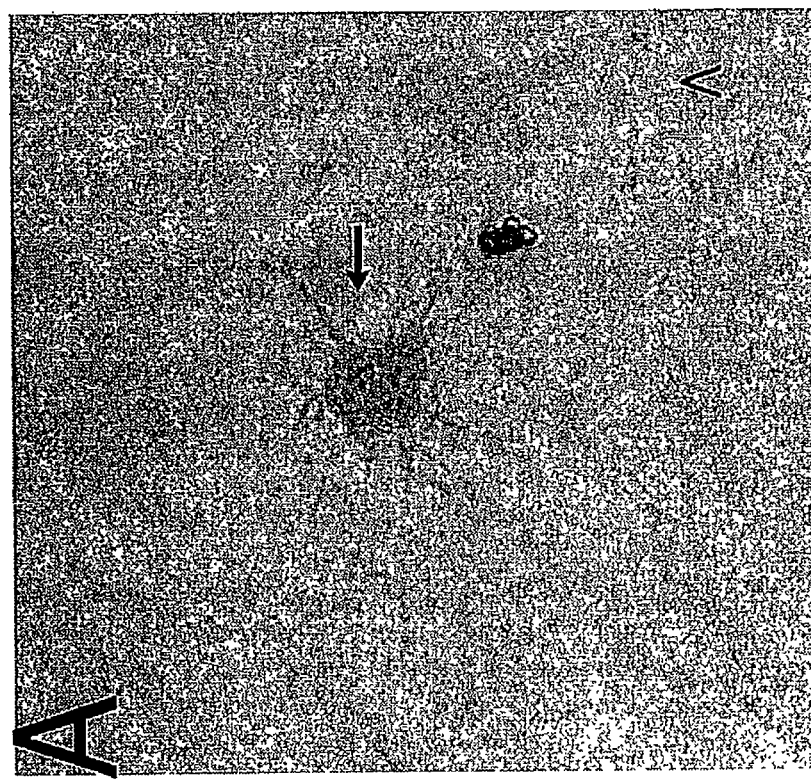
FIG. 4A is an image depicting NeuN expression in rMSC-derived neurons using a monoclonal anti-NeuN antibody (Chemicon, Temeeula, Calif.). Briefly, the data disclosed herein demonstrate that NeuN can be detected in the nucleus and surrounding cytoplasm of rMSC-derived neurons (arrow).
Figure 7B:
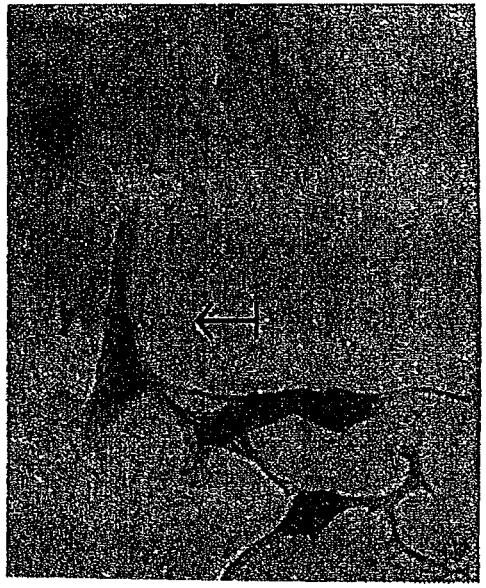
FIG. 7B is an image depicting differentiation of clonal rMSC lines. NSE-staining of individual rMSC clone #2 subjected to the differentiation protocol disclosed herein. NSE-positive cells (dark brown) are derived from each clonal line. Undifferentiated rMSCs (>) and/or transitional cells (↦) are evident in each panel. (Magnification=320×).
Figure 7D:
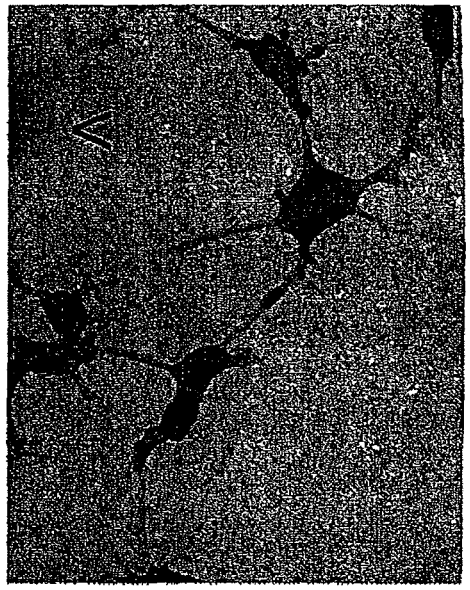
FIG. 7D is an image depicting differentiation of clonal rMSC lines. NSE-staining of individual rMSC clone #1 subjected to the differentiation protocol disclosed herein. NSE-positive cells (dark brown) are derived from each clonal line. Undifferentiated rMSCs (>) and/or transitional cells (↦) are evident in each panel. (Magnification 320×).
Figure 7A:
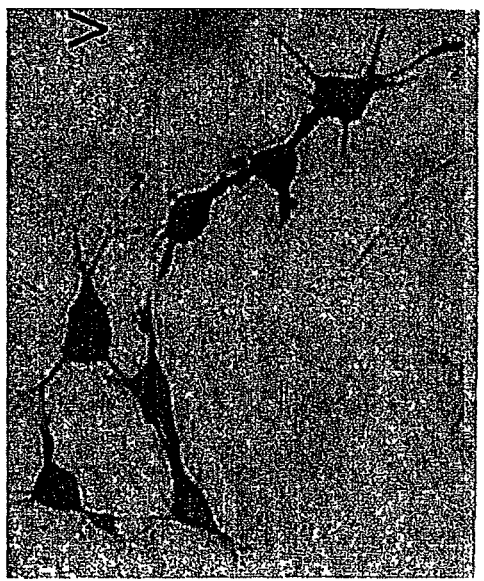
FIG. 7A is an image depicting differentiation of clonal rMSC lines. NSE-staining of individual rMSC clone #1 subjected to the differentiation protocol disclosed herein. NSE-positive cells (dark brown) are derived from each clonal line. Undifferentiated rMSCs (>) and/or transitional cells (↦) are evident in each panel. (Magnification=320×).
Figure 7C:
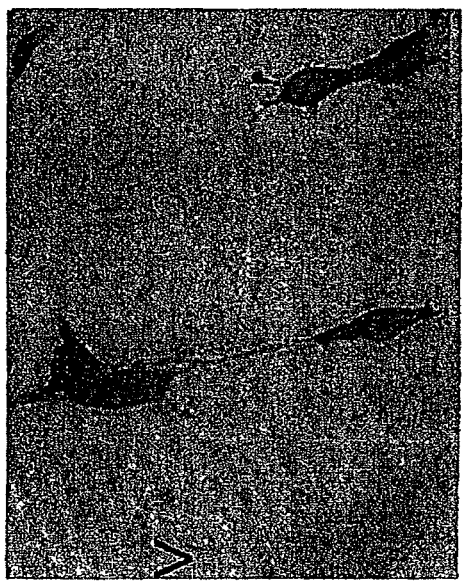
FIG. 7C is an image depicting differentiation of clonal rMSC lines. NSE-staining of individual rMSC clone #3 subjected to the differentiation protocol disclosed herein. NSE-positive cells (dark brown) are derived from each clonal line. Undifferentiated rMSCs (>) and/or transitional cells (↦) are evident in each panel. (Magnification=320×).

To further investigate neuronal characteristics, differentiated cultures were stained for NeuN, a neuron-specific marker expressed in post-mitotic cells (Sarnat et al., 1998, Brain Res. 20:88-94). A subset of cells exhibiting rounded cell-bodies and processes (arrow) stained for NeuN expression, while undifferentiated cells (<) remained NeuN-negative (FIG. 4A). Consistent with previous reports describing NeuN staining of neuronal cells (Sarnat et al., 1998, Brain Res. 20:88-94), NeuN staining was confined to the nucleus and surrounding cytoplasm of positive cells, and did not extend into the processes. Some cells exhibiting distinct neuronal morphologies did not express NeuN (↦), while neighboring cells were intensely positive (arrow) (FIG. 4B). This pattern contrasts with that established for NSE staining, where every cell exhibiting a neuronal morphology demonstrated increased NSE expression. Without wishing to be bound by any particular theory, these data suggest that a subset of NSE-positive cells are post-mitotic neurons. Also without wishing to be bound by any particular theory, it may be that the anti-oxidant properties of BME, which enhance neuronal survival in vitro (Ishii et al., 1993, Neurosci. Lett. 163:159-162), may mediate, in part, induction of neuronal differentiation in MSCs although this surprising result was unexpected based on prior studies.

Figure 9D:
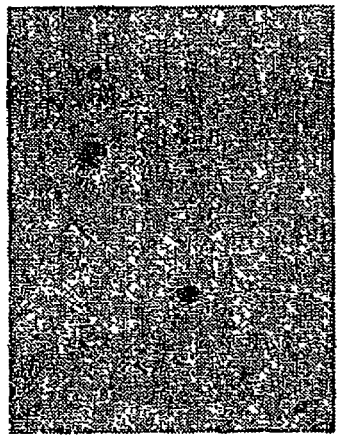
FIGS. 9A-9F, is an image depicting nestin and trkA expression in differentiating rMSC-derived neurons.
Figure 9E:
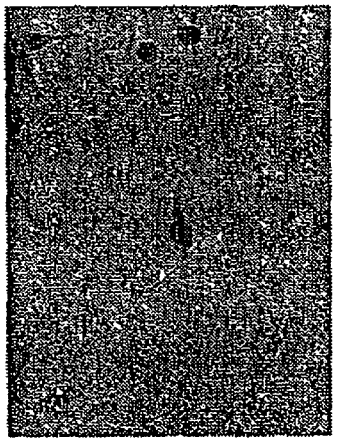
Figure 9F:
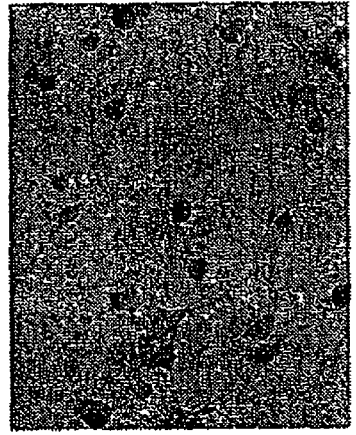
Figure 9A:
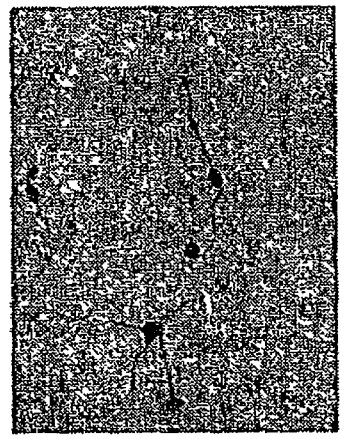
Figure 9B:
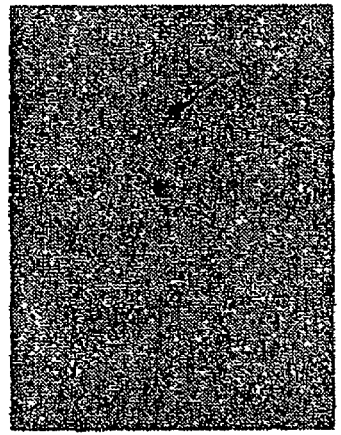
Figure 9C:
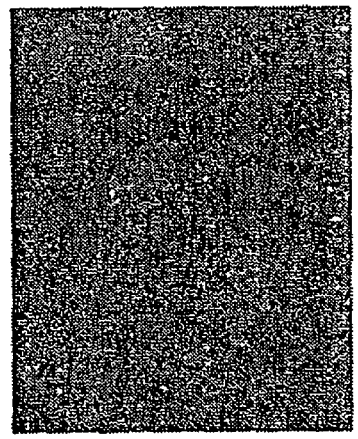

Nestin, an intermediate filament protein, is expressed in neuroepithelial neuronal precursor stem cells, with expression decreasing as the neuron matures. Experimental data shows that when the MSC-differentiated neuronal cells are stained to detect nestin, the expression of nestin decreases over time (FIGS. 9A-9C). Further, staining for trkA, a high-affinity nerve growth factor receptor which is present in neurons, demonstrates that trkA levels remain unchanged throughout the maturation process of the MSC-differentiated neuronal cell (FIGS. 9D-9F).

To begin examining the hypothesis that the anti-oxidant properties of BME mediated induction of neuronal differentiation in MSCs, rMSCs were treated with other anti-oxidants, e.g., dimethylsulfoxide (DMSO), butylated hydroxyanisole (BHA), or butylated hydroxytoluene (BHT), ascorbic acid, dimethylfumarate, n-acetylcysteine, and the like, both alone and in combination with each other. Further, treatment with the anti-oxidant dithiothreitol (DTT) in combination with BHA also induced neuronal differentiation by MSCs suggesting that DTT alone may also elicit neuronal differentiation.

Each anti-oxidant treatment (e.g., DMSO, BHA, BHT, ascorbic acid, dimethylfumarate, n-acetylcysteine, and the like, both alone and in combination) elicited neuronal morphologies with a time course similar to the effects of BME. Additionally, preliminary data suggested that treatment using about 2% (v/v) DMSO and about 200 millimolar BHA (DMSO/BHA) was preferred although a wide range of concentrations elicited neuronal differentiation.

To further characterize neuronal identity, MSCs treated with DMSO/BHA were stained for neurofilament-M (NF-M), a neuron-specific intermediate filament that helps initiate neurite elongation (Carden et al., 1987, Neurosci. 7:3489-3504). The data disclosed previously elsewhere herein demonstrated that BME treatment of MSCs caused increased expression of NF-M in cells exhibiting neuronal morphologies. Most cells displaying rounded cell bodies with processes (arrow) after DMSO/BHA exposure expressed high levels of NF-M, while flat undifferentiated cells (>) did not (FIG. 5A). Pre-adsorption of NF-M antibody with purified NF-M protein abolished staining (FIG. 5B), establishing specificity.

DMSO/BHA treated cultures were then examined for the presence of tau, a neuron-specific microtubule-associated protein expressed by differentiating neurons (Kosik and Finch, 1987, J. Neurosci. 7:3142-3153). Cells exhibiting a neuronal morphology (arrow) expressed tau protein in the cell body as well as in the processes (*), while undifferentiated flat cells were tau-negative (<) (FIGS. 5C and 5D). The data disclosed herein indicate that the method described herein induce neuronal differentiation of marrow stromal cells.

Activity-Dependent Synaptic Vesicle Recycling

To further characterize neuronal properties, cultures were treated with the styryl dye FM1-43, which labels the outer leaflet of synaptic vesicles upon activity-dependent transmitter release (Betz and Bewick, 1992, Science 255:200-203; Betz et al., 1992, J. Neurosci. 12:363-375; Diefenbach et al., 1999, J. Neurosci. 19:9436-9444). Exposure to depolarizing concentrations of $K^+$ resulted in fluorescent labeling of growth cones (↦), suggesting that the cells were recycling synaptic vesicles consequent to activity-dependent transmitter release.

Clonal Analysis

To determine whether individual rMSCs exhibit stem cell characteristics of self-renewal and pluripotentiality, individual clones were analyzed. To establish clones, rMSCs were plated at approximately 10 cells per square centimeters, grown to 50-150 cells per colony, isolated with cloning cylinders, transferred to separate wells and eventually to individual flasks. Single cells replicated as typical rMSCs and differentiated into NSE-positive neurons after BME treatment.

Analysis of four distinct clonal lines is shown in FIG. 7A-7D. Each individual clone generated refractile, process-bearing, NSE-positive cells following BME treatment. Undifferentiated rMSCs (>) and transitional cells (↦) were evident in each clonal line. Therefore, clones derived from a single cell can give rise to both rMSCs and neurons, indicating stem cell characteristics.

Human Stromal Cells Differentiate into Neurons

The neuronal potential of MSCs was not unique to rodents as demonstrated by the following experiments using MSCs obtained from humans (hMSCs). hMSCs were isolated from a healthy adult donor and grown in vitro (Bjornson et al., 1999, Science 283:534-537). hMSCs resembled their rodent counterparts, growing as large flat cells in the undifferentiated state.

Cells from passage two were subjected to the neuronal differentiation protocol and stained for NSE or NF-M expression. After BME treatment, hMSCs attained neuronal characteristics and increased NSE expression in a time frame similar to that observed for rMSCs. Contracted cell bodies elaborated processes and stained strongly for NSE expression within 3 hours (FIGS. 8A and 8B). Transitional cells were also evident (↦). Many processes elaborated by hMSC-derived neurons exhibited terminal bulbs (arrow in 8B), which may represent growth cones. Growth cone morphologies with filopodial extensions (↔) were clearly evident on the processes elaborated by paired neurons depicted in the image in FIG. 8C. These cells also expressed NF-M, consistent with their neuronal differentiation (FIG. 8D).

The data disclosed herein demonstrate that rat and human MSCs retain the capacity to differentiate into non-mesenchymal derivatives, specifically neurons, suggesting that intrinsic genomic mechanisms of commitment, lineage restriction and cell fate are mutable. Environmental signals apparently can elicit the expression of pluripotentiality that extends well beyond the accepted fate restrictions of cells originating in classical embryonic germ layers. These adult cells are both self-renewing and multipotential (Owens and Friedenstein, 1988, Ciba Foundation Symp. 136, Chichester, U.K. pp. 42-60; Prockop, 1997, Science 276; 71-74; Ferrari et al., 1998, Science 279:1528-1530; Caplan, 1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell. Physiol. 176:57-66; Pittenger et al., 1999, Science 284:143-147), thereby fulfilling many of the criteria of a stem cell population.

To the best of Applicants' knowledge, this is the first report that peripheral mesenchymal cells can differentiate into neurons in vitro. Further, the present invention provides, for the first time, methods of directing differentiation of MSCs into neuronal cells in vitro. MSCs are useful in the treatment of a wide variety of neurologic diseases disorders and conditions, and these cells offer significant advantages over other so-called "stem" cells. That is, bone marrow cells are readily accessible, obviating the risks of obtaining neural stem cells from the brain, and provide a renewable population which can be expanded in vitro thereby allowing complex gene manipulations to be performed for ex vivo gene therapy and/or for cell therapy for CNS diseases, disorders or conditions that require administering cells to a CNS site. Furthermore, autologous transplantation overcomes the ethical and immunologic concerns associated with the use of fetal tissue. Moreover, MSCs grow rapidly in culture, precluding the need for immortalization, and differentiate into neurons exclusively using the protocols disclosed herein.

Expression of Neuronal Proteins in MSC-Differentiated Neuronal Cells

The data disclosed herein demonstrates that neuronal cells differentiated from MSCs as described herein express various neuron-related proteins. For example, immunocytochemical analysis of these differentiated neurons revealed the expression of beta-3 tubulin. Further, TOAD-64, a neuronal protein of unknown function, is also detectable using immunocytochemical techniques, as well as synaptophysin, which is associated with synapses and synaptic vesicles. Using polyclonal and monoclonal antibody-based procedures, these cells have been demonstrated to express choline acetyltransferase, an enzyme responsible for the synthesis of the neurotransmitter acetylcholine. Finally, tyrosine hydroxylase, the rate-limiting enzyme in catecholamine biosynthesis, was also detected immunocytochemically in a population of these differentiated neurons.

It is apparent that due to the presence of these neuronal gene products, the differentiated neurons may be therapeutically beneficial to treating those diseases affecting cholinergic and catecholaminergic systems, such as, for example, Alzheimer's disease, Parkinson's disease, or schizophrenia.

Transplantation of the Differentiated Neurons to Experimental Animals

The differentiated neurons generated as described herein, were further tested to determine their viability in vivo. The neurons were transplanted, using sterile technique and known and accepted neurosurgical procedures (1997, Grill et al.; 1995, Gage et al., 1994, Dunnett et al.), into the hippocampus or striatum of the brain or the dorsal horn of the spinal cord of individual rats. Each rat received a transplant to one of the aforementioned areas. The rats were returned to their cages and received standard postoperative care with access to food and water ad libatum.

To determine whether neuron viability was maintained in vivo, a post-operative study of the rats receiving the transplant was conducted. Rats receiving the neuronal transplant were examined 42 days after the transplantation operation took place. Using fluorescence microscopy to detect bisbenzimide-positive transplanted cells, histologic studies of the hippocampal and striatal regions of the brain revealed that the transplanted neurons survived in the hippocampus. This result indicates that long-term survival of the transplanted, differentiated neurons is possible. An examination of the rats receiving the transplanted neurons in the dorsal horn of the spinal cord demonstrated a survival period of at least three days. Further, the processes of the transplanted neurons in this area grew to at least two to three times in length than the cell body diameter.

As is evident from these results, transplanted, differentiated neurons express many neuronal proteins, retain viability in vivo, and seemingly exert no detectable deleterious effect on the living animal. As a result, these neurons create a potential therapeutic treatment for a variety of brain and spinal cord diseases, including, but not limited to, Alzheimer's disease, Parkinson's disease, Schizophrenia, and spinal cord injury resulting from trauma or degeneration.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inducing differentiation of an isolated marrow stromal cell into a neuronal cell, comprising contacting the isolated marrow stromal cell with at least one growth factor selected from the group consisting of platelet-derived growth factor and fibroblast growth factor 2 and in the absence of further growth or differentiating factors, thereby inducing differentiation of the isolated marrow stromal cell into a neuronal cell.

2. The method of claim 1, wherein said isolated marrow stromal cell is a human cell.

3. A method of producing an isolated neuronal cell, comprising isolating a marrow stromal cell, contacting the marrow stromal cell with a neuronal differentiation-inducing compound, wherein the neuronal differentiation-inducing compound is selected from the group consisting of platelet-derived growth factor and fibroblast growth factor 2 and in the absence of further growth or differentiating factors, and wherein the compound induces the isolated marrow stromal cell to differentiate into an isolated neuronal cell, thereby producing said isolated neuronal cell.

\* \* \* \* \*